United States Patent
Mouchawar

(10) Patent No.: US 6,445,951 B1
(45) Date of Patent: Sep. 3, 2002

(54) IMPLANTABLE CARDIAC STIMULATING DEVICE INCORPORATING HIGH FREQUENCY LOW AMPLITUDE LEAD IMPEDANCE MEASUREMENT

(75) Inventor: Gabriel Mouchawar, Newhall, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/415,619

(22) Filed: Oct. 12, 1999

(51) Int. Cl.⁷ .................................................. A61N 1/37
(52) U.S. Cl. .......................................................... 607/28
(58) Field of Search ............................... 607/8, 17, 20, 607/24, 28

(56) References Cited

U.S. PATENT DOCUMENTS

| | | |
|---|---|---|
| 4,840,177 A | 6/1989 | Charbonnier et al. |
| 4,993,423 A | 2/1991 | Stice |
| 5,020,541 A | 6/1991 | Marriott |
| 5,058,583 A | 10/1991 | Geddes et al. |
| 5,088,489 A | 2/1992 | Lerman |
| 5,097,830 A | 3/1992 | Eikefjord et al. |
| 5,111,813 A | 5/1992 | Charbonnier et al. |
| 5,201,865 A | 4/1993 | Kuehn |
| 5,215,081 A | 6/1993 | Ostroff |
| 5,350,403 A | 9/1994 | Stroetmann et al. |
| 5,817,136 A | * 10/1998 | Nappholz et al. ............. 607/17 |

* cited by examiner

Primary Examiner—Jeffrey R. Jastrzab

(57) ABSTRACT

An implantable cardiac stimulating device incorporating high voltage leads for the delivery of cardioversion or defibrillation waveforms is provided. The implantable cardiac stimulating device incorporates a lead impedance measurement which measures the impedance of the high voltage lead using a high frequency, e.g., 20 KHz or higher, low amplitude, e.g., 500 microamps or lower, signal which results in a lead impedance measurement that has a high degree of correlation to the lead impedance that would occur when the high voltage defibrillation or cardioversion waveform is applied to the heart from the electrode. The implantable cardiac stimulating device is further configured to take corrective action upon the detection of a lead having a high or low impedance that suggests a broken, shorted or damaged lead.

39 Claims, 4 Drawing Sheets

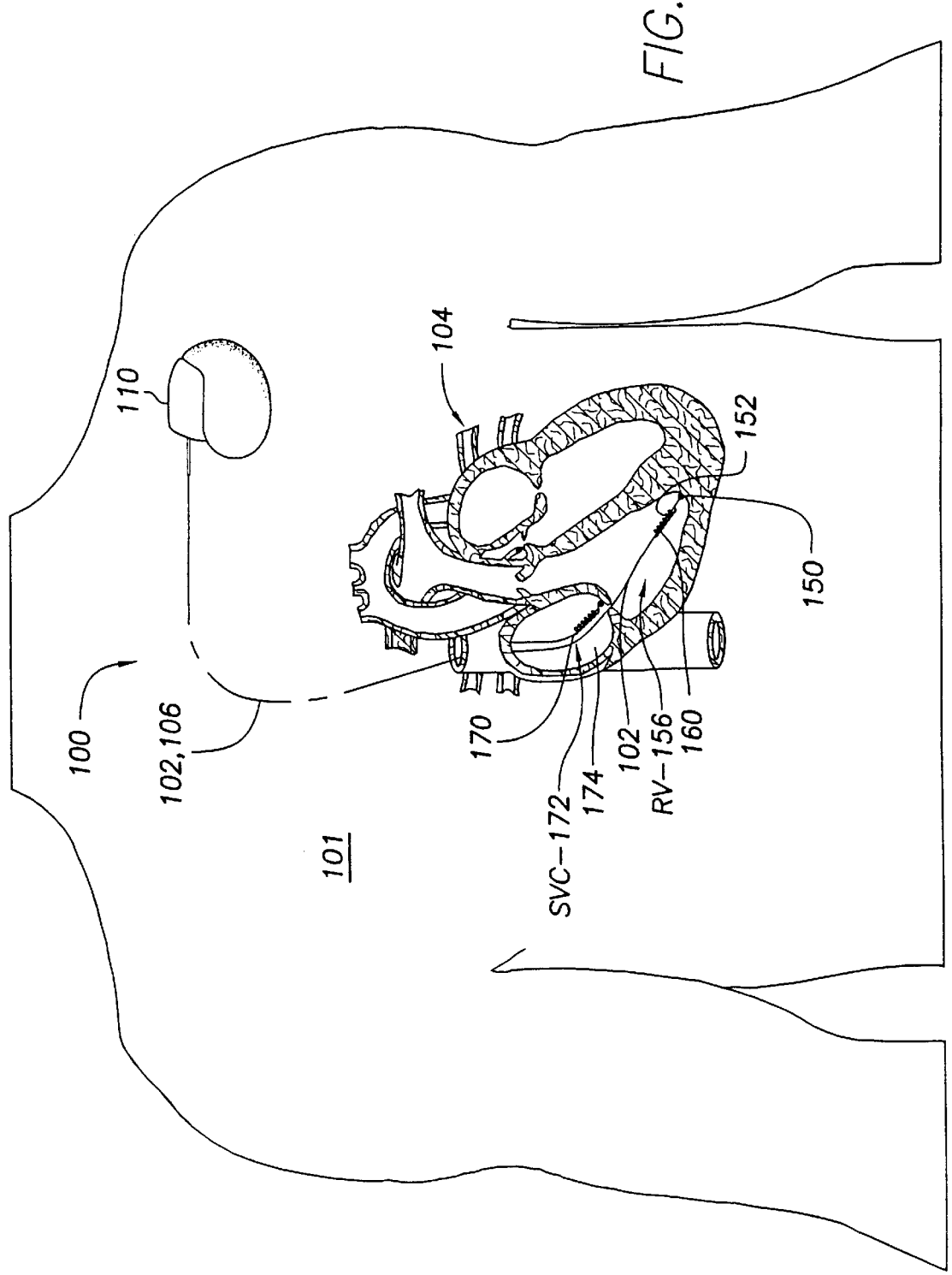

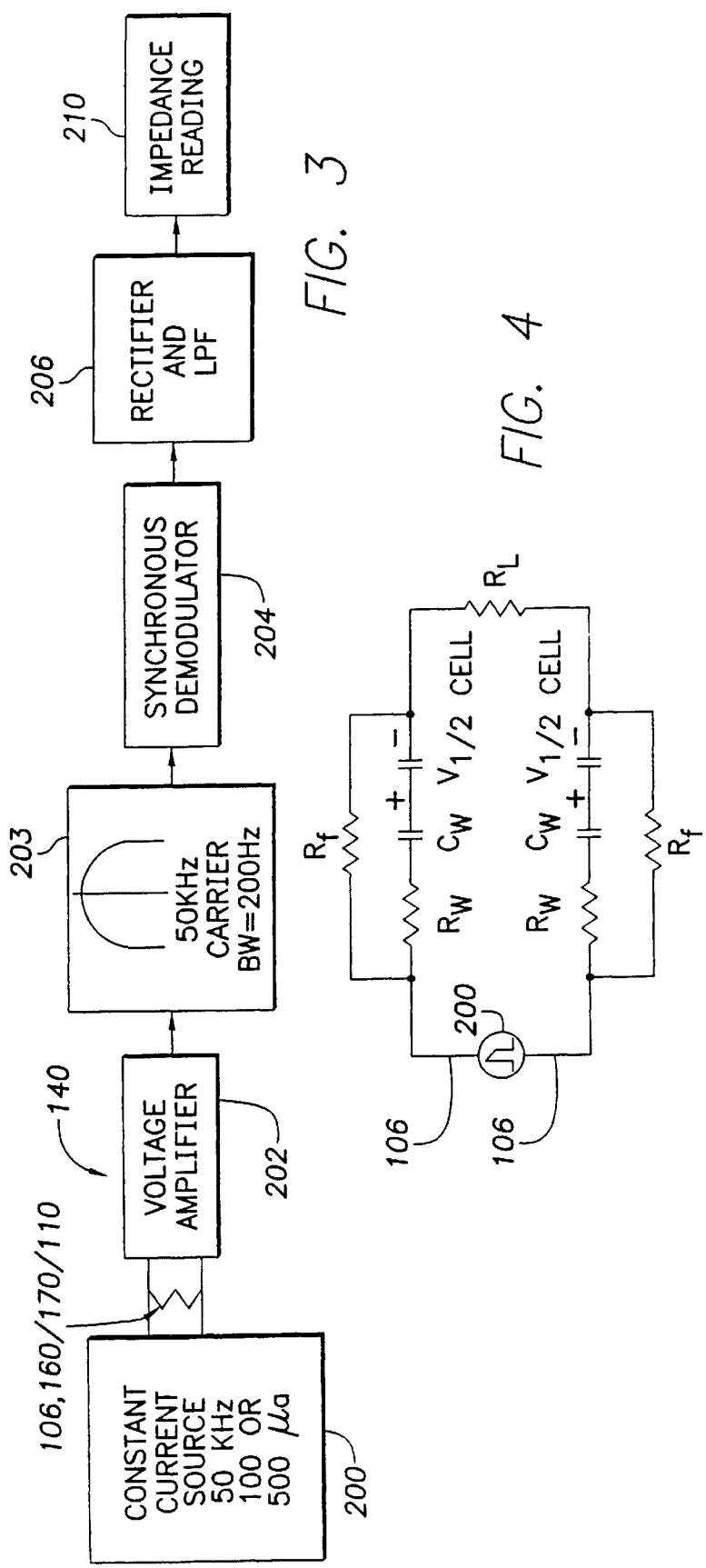

IMPLANTABLE CARDIAC STIMULATING DEVICE INCORPORATING HIGH FREQUENCY LOW AMPLITUDE LEAD IMPEDANCE MEASUREMENT

FIELD OF THE INVENTION

The present invention relates to implantable cardiac stimulating devices, including devices having defibrillation or cardioversion leads and, more particularly, concerns an implantable cardiac stimulating device that is adapted to obtain an accurate impedance measurement of the cardioversion or defibrillation lead using a low amplitude, high frequency signal.

BACKGROUND OF THE INVENTION

Implantable cardiac stimulating devices are devices that are adapted to be implanted within the body of a patient so that therapeutic electrical stimulation can be provided to the patient's heart to regulate heart function. These types of devices include well known pacemakers or implantable cardioverter defibrillators (ICDs) or devices that include the functionality of both a pacemaker and an ICD.

Typically, these devices include a control unit, having a microprocessor, and one or more leads that are adapted to be positioned adjacent the walls of the heart. The control unit typically receives sensory input about the function of the heart and, when the input is indicative of a heart arrhythmia, the control unit then provides an appropriate therapeutic electrical stimulation to the heart via the leads. The therapeutic electrical stimulation can, for example, consist of a low voltage pacing pulse to ensure the heart is beating correctly, or can include a high-voltage waveform that is adapted to terminate a particular form of cardiac arrhythmia, such as ventricular fibrillation.

One particular problem with implantable cardiac stimulating devices is that the lead that is adapted to provide the electrical stimulation to the heart can become damaged. In many instances, the leads are implanted into the chambers of the heart. In this environment, the leads are continuously subjected to forces as a result of the beating of the heart. Over time, the leads can become damaged or even broken such that the delivery of the therapeutic electrical stimulation can be impaired. This is a very serious problem with ICDs that are adapted to terminate more serious forms of cardiac arrhythmia.

For example, if the ICD is adapted to recognize and provide a therapeutic shock to the heart upon the occurrence of ventricular fibrillation, a damaged or broken lead may result in the ICD being unable to provide a waveform of sufficient magnitude to terminate the ventricular fibrillation. As is generally understood, ventricular fibrillation is characterized by the random depolarization of the cardiac cells in the ventricle. The random depolarization of heart cells results in little or no blood being pumped by the heart which can ultimately cause the death of the patient. Typically, upon recognizing ventricular fibrillation, the ICD provides a high voltage, e.g., 550 volt, biphasic waveform to the heart that simultaneously depolarizes the majority of the heart cells so that the cells can simultaneously repolarize and, desirably, begin depolarizing in a more synchronous fashion.

An increase in the impedance of the lead that is to deliver the defibrillation waveform may result in a degradation in the amplitude of the waveform such that the waveform may be unable to terminate the arrhythmia. In extreme cases, a broken lead may result in the ICD being unable to deliver any high voltage waveform to the heart. Consequently, it is desirable to be able to periodically assess the impedance of a high voltage defibrillation or cardioversion lead to ensure that the lead will be able to adequately provide the high voltage waveform to terminate a life threatening arrhythmia.

To address these particular problems, some implantable cardiac devices of the prior art have instituted procedures whereby the impedance of leads are periodically measured. Once such example is provided by U.S. Pat. No. 5,549,646 to Katz et al. The device disclosed in this patent includes an impedance measurement circuit that has a voltage source which applies a voltage to an ICD lead so that impedance measurement of the ICD lead can be obtained. The impedance measurement of the ICD lead can then be compared to a reference value to determine whether the lead impedance has exceeded a predetermined amount. However, the circuit disclosed in this patent uses a low voltage, low frequency source in order to determine the lead impedance. While the use of the low voltage source reduces the amount of limited power that is consumed in order to test the impedance, this low voltage source will give rise to an impedance measurement that does not necessarily correspond to the impedance that would occur when the high voltage defibrillation or cardioversion waveform is applied across the leads.

Specifically, the lead impedance at voltages below 100 volts is a non-linear function of the electrode surface area and the amplitude of the current passing through the electrode. The non-linearity of the relationship between the impedance, the surface area and the current is due to the capacitive polarizing effects and the electrochemical reactions at the lead-tissue interface. The impedance that is obtained using the lead impedance measurement circuit of U.S. Pat. No. 5,549,646 does not always yield a measurement value that can be used to determine what the corresponding impedance would be when a high voltage cardioversion or defibrillation waveform is applied to the heart. As a consequence, using low voltage, low frequency waveforms generally does not result in an impedance measurement that accurately reflects the actual lead impedance. Hence, the impedance reference values have a degree of error which may result in the impedance measurement circuit obscuring subtle changes in impedance which precede total lead failure, disabling effective high voltage therapy to the heart to correct an arrhythmia.

As an alternative, the impedance can also be measured using a high voltage waveform similar to the cardioversion or defibrillation waveform. However, for testing purposes this is impractical as it would cause tremendous discomfort to the patient, create a risk of inducing unwanted cardiac arrhythmias and consume a significant amount of limited battery power.

Therefore, there is a need for an implantable cardiac stimulating device that can periodically assess the status of the leads and the ability of the leads to deliver a high voltage therapeutic waveform. To this end, there is a need for an implantable cardiac stimulating device that is capable of obtaining an impedance measurement using a low voltage waveform that is indicative of the corresponding impedance that will occur when a high voltage therapeutic waveform is applied to the heart from the leads to correct an arrhythmia.

SUMMARY OF THE INVENTION

The aforementioned needs are satisfied by the implantable cardiac stimulating device of the present invention which is comprised of a control unit that is adapted to be implanted within the heart of a patient and at least one high voltage lead that is adapted to be positioned adjacent the heart so as to apply high voltage cardioversion or defibrillation shocks to the heart. The control unit also includes an impedance measurement circuit which is adapted to be able to provide a low amplitude, high frequency impedance measurement signal to the lead and then measure the resulting electrical response on a second electrode so that an impedance measurement can be obtained using a low amplitude signal. The resulting impedance measurement has a high correlation to the actual impedance that would occur when a high voltage cardioversion or defibrillation waveform is applied to the lead. In this way, the impedance of the particular lead can be accurately measured without consuming excess power and without being felt by the patient, while still obtaining a measurement that has a high correlation to the impedance that would actually occur when the high voltage cardioversion or defibrillation waveform is applied to the lead.

In one embodiment, a 50 KHz sinusoidal constant current signal having a magnitude of approximately either 100 or 500 microamps, peak to peak, is enabled by a microprocessor in the control unit so as to provide the impedance measurement signal between two electrodes for less than one second to a defibrillation lead. The resulting voltage between these electrodes, which can comprise any of a number of electrodes including the casing of the implantable cardiac device, is then measured in order to obtain a measurement of the impedance of the lead. Applying such a high frequency, low amplitude current for a period of less than one second results in the ability to test the impedance and obtain an impedance measurement that is within a few percent of the impedance that would be measured when a high energy (e.g., 16 joule) defibrillation waveform is applied to the heart. The use of such a high frequency signal avoids the polarization error that would otherwise occur in the measurement of the impedance.

It will be appreciated that the implantable cardiac device incorporating the impedance measurement circuit of the present invention is capable of measuring the impedance and providing a very accurate indication of the impedance that will occur upon the delivery of a high voltage cardioversion or defibrillation waveform without requiring the consumption of a large amount of limited battery power and without being felt by the patient. These and other objects and advantages of the present invention will become more fully apparent from the following description taken in conjunction with the accompanying drawings.

BRIEF DESCRIPTION OF THE DRAWINGS

FIG. 2 is a perspective view of the implantable cardiac device of FIG. 1 as implanted in the body of a patient;

FIG. 3 is a block diagram illustrating the components of the impedance measurement circuit of the implantable cardiac stimulating device of FIG. 1 in greater detail;

FIG. 4 is a circuit diagram illustrating the equivalent circuit between any two electrodes of FIG. 1 and the heart;

FIG. 5 is a table illustrating data obtained from an animal experiment using the impedance measurement circuit of FIG. 3.

DETAILED DESCRIPTION OF THE PREFERRED EMBODIMENT

Figure 1:
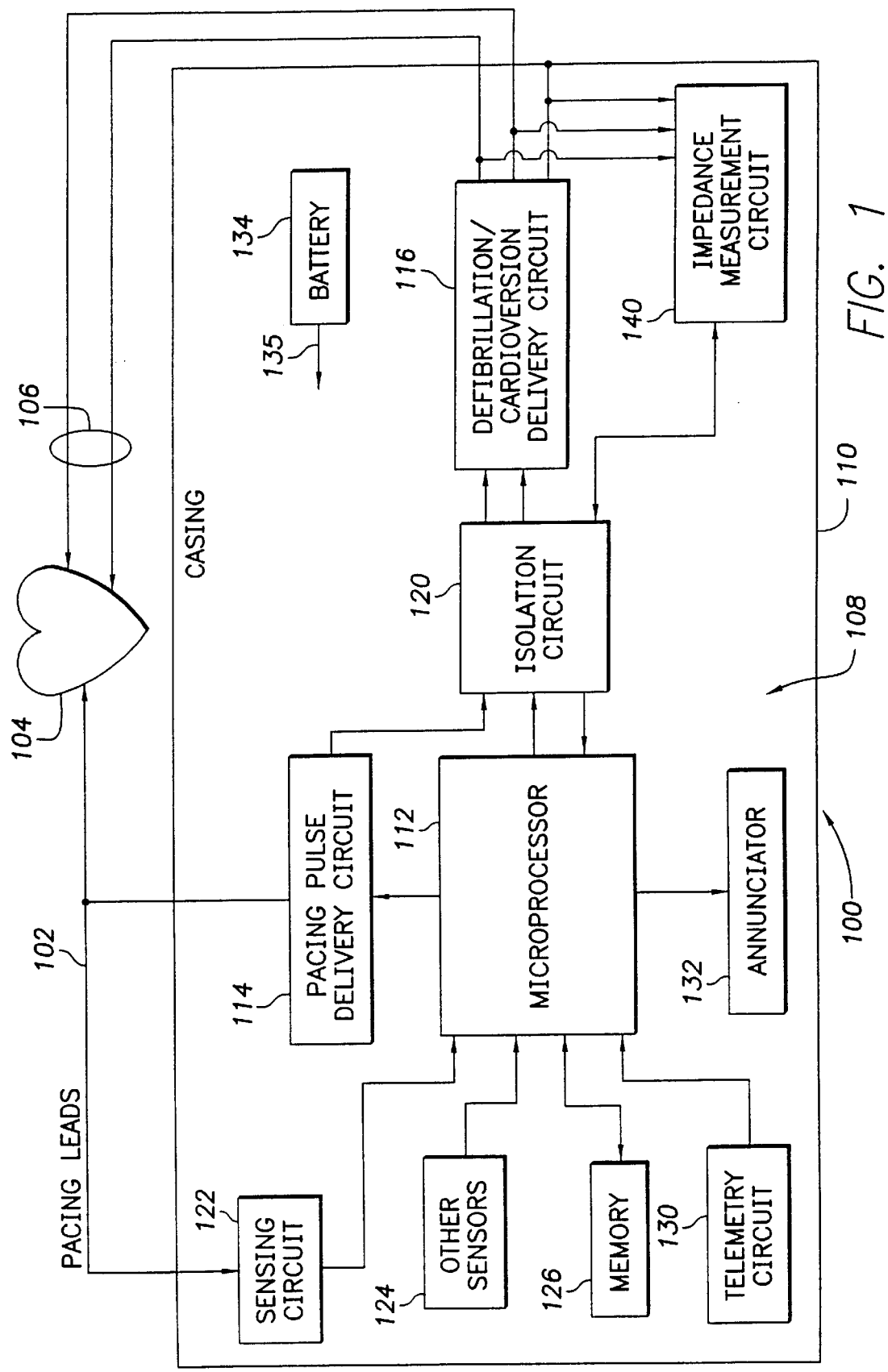
FIG. 1 is a block diagram of an implantable cardiac stimulating device incorporating an impedance measurement circuit of the present invention.

Reference will now be made to the drawings wherein like numerals refer to like parts throughout. FIG. 1 is a block diagram of an exemplary implantable cardiac stimulating device 100 of the preferred embodiment. The implantable cardiac stimulating device 100 is capable of providing both pacing pulses and higher voltage waveforms, such as cardioversion or defibrillation waveforms.

In particular, the implantable cardiac stimulating device 100 has one or more pacing leads 102 that are adapted to be positioned adjacent the heart 104 in a position where the delivery of pacing pulses will result in a paced beat response of a chamber of the heart 104. One typical place for the location of the tip of the pacing leads is in the apex of the right ventricle of the heart 104 as shown in FIG. 2.

Similarly, the implantable cardiac stimulating device 100 also includes one or more high voltage leads 106 that are adapted to supply either cardioversion or defibrillation waveforms to the heart 104 in a manner that is known in the art. The high voltage leads 106 typically terminate in coils that are implanted in various locations within the heart 104, such as the right ventricle or the superior vena cava, that will be selected so that the delivery of high voltage waveforms will terminate a tachycardia or fibrillation episode of the heart 104. The placement of exemplary pacing leads 102 and the high voltage coils will be described in greater detail in reference to FIG. 2 hereinbelow.

The implantable cardiac stimulating device 100 also incorporates a control unit 108 that is positioned within a casing 110 (typically electrically conductive). The control unit 108 incorporates control circuitry that is adapted to deliver either the pacing pulses or the high voltage waveforms to the heart 104 via the leads 102 or 106, respectively. In this embodiment, the control unit 108 incorporates a microprocessor 112 that is adapted to induce the delivery of the pacing pulses via a pacing pulse delivery circuit 114 to the pacing leads 102 in a manner that is known in the art.

Similarly, the microprocessor 112 is adapted to induce a defibrillation/cardioversion delivery circuit 116 to deliver an appropriate high voltage (e.g.. 700–800 volts peak), high energy (e.g., 32 joule) waveform/signal to the heart 104 via the high voltage leads 106 to terminate a tachycardia or fibrillation of the heart 104 in a manner that is also known in the art. As is also shown in FIG. 1, the high voltage defibrillation/cardioversion delivery circuit 116 is typically isolated from the low voltage microprocessor 112, sensing circuit 122, sensors 124, and the pacing pulse delivery circuit 114 via an isolation circuit 120. The configuration of the isolation circuit 120 can be any of a number of configurations known in the art.

The microprocessor 112 induces the pacing pulse delivery circuit 114 or the defibrillation/cardioversion delivery circuit 116 to provide appropriate electrical stimulations to the heart 104 via the leads 102, 106, respectively, based upon inputs from various sensors. For example, the microprocessor 112 receives a sensor input that is indicative of the activity of the heart from the sensing circuit 122. In this embodiment, the sensing circuit 122 is connected to the pacing lead 102 such that the pacing leads 102 can provide an intracardiac electrogram (IEG) to the microprocessor 112 in a manner that is known in the art. In this way, the microprocessor 112 can receive a signal that is indicative of the actual heart function. The microprocessor 112 is adapted to interpret the signal to recognize various cardiac arrhythmias so that the microprocessor 112 can provide an appropriate stimulation from either the pacing pulse delivery circuit 114 or the defibrillation/cardioversion delivery circuit 116 in a manner that is generally known in the art.

The microprocessor 112 may also receive signals from other sensors 124, such as an acceleration sensor, a minute ventilation sensor, and the like. In this way, the microprocessor 112 is able to optimize the delivery of either pacing pulses or high voltage defibrillation/cardioversion waveforms to the heart 104 to appropriately regulate heart function.

The control unit 108 in this embodiment also incorporates a memory 126 that preferably contains both operating instructions for the microprocessor 112 and also data that is to be stored in the memory 126 by the microprocessor 112. In this embodiment, the data can preferably be subsequently accessed by a treating physician via a telemetry circuit 130 in a manner that is known in the art. The data that is stored within the memory 126 for subsequent access by a treating physician may include operating parameters of the implantable cardiac device 100 or observed patient parameters, e.g., responses to particular waveforms, recordings of IEG signals during periods of cardiac arrhythmia, etc.

In this embodiment, the control unit 108 also preferably incorporates an annunciator 132 that can be activated by the microprocessor 112 so as to provide the patient with a warning. In one embodiment, the annunciator 132 may be comprised of a piezo-electric buzzer or the like that will emit an audible tone to the patient to alert the patient to the existence of a particular problem without stimulating the heart 104. In another embodiment, the annunciator may comprise circuitry that will enable the microprocessor 112 to induce the delivery of a series of electrical stimulations to the patient that are adapted to be felt by the patient so that the patient is aware of the problem but without stimulating the heart 104. Alternatively, an annunciator function may also comprise storing data in the memory 126 indicative of the problem so that a treating physician can subsequently review the data and be advised of the potential problem during a follow up visit.

Each of the components of the implantable cardiac stimulating device 100 is powered by a battery 134 via power path 135. The use of a limited power supply, such as a battery, to power the device 100 imposes significant design constraints on the implantable cardiac stimulating device 100. For example, it is generally desirable to limit the consumption of battery power for sensory measurements to preserve the operational longevity of the device. In this way, the limited battery power is generally conserved for the delivery of therapeutic waveforms to the heart 104.

This embodiment of the control unit 108 also incorporates an impedance measurement circuit 140 that is adapted to measure the impedance of the high voltage leads 106 to determine whether the impedance of the high voltage leads 106 is indicative of a particular problem with these leads. As will be discussed in greater detail below, the microprocessor 112 is adapted to induce the impedance measurement circuit 140 to provide a high frequency, low amplitude signal to the leads 106 and measure the resulting electrical response on a return electrode so as to be able to obtain an impedance of the lead 106 and any associated shocking coil.

This impedance measurement has a high correlation to the impedance that would otherwise occur when a high voltage waveform is applied by the high voltage lead 106 to terminate a cardiac arrhythmia. As is understood in the art, the impedance of a lead that occurs upon the delivery of a high voltage defibrillation or cardioversion waveform is not linearly related to the impedance that would be measured applying a low voltage, low frequency waveform across the lead. This lack of a linear relationship is due to the polarization effects that occur at the interface between the electrode and the surrounding tissue/electrolyte. In effect, there is capacitive coupling between the current source and the heart environment such that the use of a low voltage, low frequency waveform results in an impedance measurement which is highly affected by the capacitive coupling due to the polarization effects.

To overcome this problem, the impedance measurement circuit 140 incorporates a high frequency, low amplitude current source. This current source is capable of providing a signal that results in an impedance measurement that has a high correlation to the impedance that would occur on the high voltage lead 106 when the high voltage defibrillation or cardioversion waveform is applied to the heart 104.

FIG. 2 illustrates one configuration of the implantable cardiac stimulating device 100 as it is implanted within the body of the patient 101. Specifically, in this embodiment, the casing 110 of the implantable cardiac stimulating device 100 is implanted within the body of the patient under the pectoral muscle of the patient 101 in a manner that is known in the art. The leads 102, 106 are inserted into a vein, such as the subclavian vein, and the leads 102, 106 are guided into the superior vena cava (SVC) 172, the right atrium 174 and the right ventricle 156 in the manner shown in FIG. 2. In this embodiment, the pacing lead 102 terminates in a pacing tip 150 that is implanted adjacent the apex 152 of the right ventricle 156 of the heart 104. The high voltage leads 106 terminate in an RV shocking electrode or coil 160 that is positioned within the right ventricle 156 of the heart 104 and into an SVC shocking electrode or coil 170 that is positioned within the superior vena cava 172 of the heart 104 superior to the right atrium 174 of the heart 104.

The implantation of the pacing tip 150, the RV shocking coil 160, and the SVC shocking coil 170 is accomplished in a manner that is generally known in the art. The pacing tip 150 is adapted to deliver pacing pulses to the apex 152 of the right ventricle 156 to induce a paced beat response to the heart 104. Both the RV coil 160 and the SVC soil 170 are adapted to provide high voltage waveforms to the heart 104 so as to terminate cardiac arrhythmias, such as ventricular fibrillation or atrial fibrillation.

It will be appreciated that, while FIGS. 1 and 2 have described an implantable cardiac stimulating device that incorporates the functionality of both a pacemaker and an implantable cardioverter defibrillator (ICD), the impedance measurement circuit 140 of the preferred embodiment can be used with implantable cardiac stimulating devices that incorporate only the functionality of an ICD. Hence, the implantable cardiac stimulating device 100 shown in FIGS. 1 and 2 is simply illustrative of one of a number of implantable cardiac stimulating devices that can incorporate the impedance measurement circuit 140 of the present invention.

As will be described in greater detail below in reference to FIGS. 3–6, the impedance measurement circuit 140 of the present invention is adapted to measure the impedance between two high voltage leads 106 with the associated shocking coils (electrodes) 160, 170 or the casing 110 by sending a high frequency, low amplitude current signal and then measuring the resulting voltage on the electrodes (or casing). In tests performed by the applicant, sending such a signal results in an impedance measurement that very closely corresponds to the impedance measurement of the lead 106 and the associated electrode 160, 170 when a high voltage defibrillation or cardioversion waveform is applied.

FIG. 3 is a block diagram which illustrates the impedance measurement circuit 140 in greater detail. The impedance measurement circuit 140 includes a constant current source 200 that provides a low amplitude, e.g., approximately 500 microamps or less, high frequency, e.g., greater than 20 KHz, output signal. In this embodiment, the current source 200 preferably provides either a 100 microamp or a 500 microamp current at 50 KHz. As will be described in greater detail below, when the microprocessor 112 enables the impedance measurement circuit 140, the current source 200 emits a 100 or 500 microamp measurement signal at 50 KHz for a preselected period of time, e.g., less than one second. This measurement signal is applied between any two electrodes 160, 170 or the casing 110 and the resulting electrical voltage is then measured by the impedance measurement circuit 140. Preferably, the second electrode consists of the electrode 170 which forms the return electrode when a defibrillation or cardioversion waveform is applied to the heart 104 by the high voltage leads 106 so that the impedance measured by the impedance measuring circuit 140 corresponds to the impedance that would occur when a cardioversion or defibrillation waveform is emitted by the same high voltage lead 106 and associated electrode 160, 170.

The voltage between the shocking electrodes 160, 170 is then amplified by an amplifier 202. The resulting voltage has a high frequency due to the use of a 50 KHz measurement signal. Accordingly, band pass filter 203 with a center frequency of the carrier frequency, i.e., 50 KHz, is used to process the signal. The purpose of this band pass filter is to reject erroneous signals that are not modulated at the carrier frequency. Specifically, it rejects any signal offset due to asymmetric ½ cell potentials. A synchronous demodulator 204 is then used to synchronously demodulate the band-passed signal. The synchronous demodulator 204 is used to discard the carrier, e.g., 50 KHz, and obtain only the modulating signal representing the impedance signal. The synchronous demodulator 204 then provides a signal to a rectifier and filter circuit 206. Preferably, the rectifier and filter circuit 206 includes a low pass filter that will primarily pass only the synchronously demodulated signal that is between approximately 0 to 100 Hz and, more preferably, is between 0 to 20 Hz. The resulting signal contains three components. The first is the D.C. component of the signal. This represents the bulk tissue resistance between the shocking electrodes. The second is the changes to the bulk impedance due to respiration. The third is the change of the bulk resistance due to cardiac activity which can be used as a hemodynamic signal to indicate stroke volume. The use of this technique enables a good measurement while still only injecting a small amount (i.e., 500 microamps or less) of current (and corresponding voltage) into the electrodes. Modulating the signal at the carrier frequency enables the rejection of most noise signals that are not at 50 KHz. Examples of these rejected noise signals include 50 or 60 Hz power line noise and intrinsic cardiac electrograms. It will be appreciated that the impedance reading unit 210 will provide both a varying signal that has a mean or average value and also changes between a maximum and minimum value over the time period of the measurement signal that is supplied by the current source 200. Consequently, the microprocessor 112 will receive both a mean or average impedance value that closely correlates to the actual impedance value that would occur if a high voltage waveform was applied to the heart 104 and a delta impedance value that is indicative of the change of the impedance measurement over the time period that the high frequency impedance measurement signal is applied to the leads 106 from the current source 200.

FIG. 4 is an equivalent circuit which illustrates the interconnection between the current source 200 and the load resistance of the heart 104, designated herein as $R_L$. As illustrated in FIG. 4, the equivalent circuit of the interconnection between the leads 106 and the heart 104 includes a resistance $R_f$ in parallel with a resistance $R_w$, a $V_{1/2}$ cell, and a capacitor $C_w$. As is understood in the art, the interface between the electrodes, e.g., 160, 170, that are connected in series with the heart 104 ($R_L$), is comprised of a Faraday resistance $R_f$ in parallel with a Warberg resistance $R_w$ and Warberg capacitor $C_w$ and the electrode/electrolyte ½ cell potential, the $V_{1/2}$ cell. The equivalent circuit in FIG. 4 demonstrates why the impedance measured using prior art systems that provide low voltage, low frequency waveforms does not provide a realistic approximation of the corresponding impedance of the lead that would occur when a high voltage waveform is applied to the heart.

In particular, there is capacitive coupling between the load resistance $R_L$ of the heart 104 and the voltage source that is applied to the heart 104 via the leads 106. Further, the degree of the capacitive coupling $C_w$ varies depending upon the magnitude of the waveform that is applied to the heart 104. In addition, if the electrodes are made of dissimilar metals, then the difference in the ½ cell potential between them will further introduce an error to the impedance measurement. Consequently, the impedance measured using a low voltage, low frequency waveform cannot be readily used to calculate the impedance that would occur when the high voltage waveform is applied. Consequently, the prior art systems that use low voltage waveforms are inherently inaccurate in obtaining an indication as to the magnitude of the impedance that would occur on the leads 106 when a high voltage waveform is applied.

However, as shown in the Table of FIG. 5, using the low amplitude, high frequency current source 200 results in impedance measurements that are very close to the impedance measurement that would be obtained when applying a high voltage, high energy, e.g., 16 joule, waveform to the patient's heart 104. In particular, FIG. 5 illustrates the defibrillation lead impedance that was measured when a 16 joule shock was delivered to an animal subject from a defibrillation system analyzer (DSA) and the subsequent measurements of the defibrillation lead impedance in the same animal subject when a 100 microamp, 50 KHz signal and a 500 microamp, 50 KHz signal was applied. As shown, the impedance measured with the 100 microamp, 50 KHz and the 500 microamp, 50 KHz signal corresponds very closely to the impedance that was measured when a 16 joule defibrillation shock was applied to the animal subject. In particular, the data reveals that the impedance measured with the 100 microamp signal is within one percent of the corresponding impedance measurement measured using a 16 joule high voltage defibrillation waveform. Similarly, using the 500 microamp signal, the impedance measurement was within 5 percent of the corresponding impedance measured using the 16 joule high voltage defibrillation waveform.

Hence, the use of the high frequency, low amplitude current source to measure the impedance results in impedance measurements that are very close to the actual impedance value that would occur during the delivery of a defibrillation shock. Consequently, the impedance measurement circuit 140 of the preferred embodiment provides an impedance measurement that is a very accurate predictor of the actual impedance of the lead when the high energy shock is applied.

However, very little energy is consumed to measure the impedance and the impedance measurement process is not felt by the patient. Specifically, the magnitude of the impedance measurement signal being provided in this embodiment to measure the impedance is below the sensory threshold of the patient. Moreover, the energy that is used to obtain the impedance can be given by the following calculation:

Energy=$I^2R*d$=(100 µA*0.707 RMS/peak)$^2$*50Ω*1 second

Energy=2.45 millijoules

Hence, the impedance measurement can be obtained using a limited amount of energy, e.g., less than 5 millijoules. This is particularly advantageous with implantable cardiac stimulating devices since it is generally desirable to limit the dissipation of energy from the battery so as to preserve the active life of the device.

As is also shown in the Table of FIG. 5, the impedance measurement that is obtained by the impedance measurement circuit 140 varies over the duration of the impedance measurement signal. It is understood in the art that the variation in lead impedance strongly correlates to the stroke volume of the heart. In other words, it is well understood in the prior art that, since lead impedance is inversely proportional to the amount of blood surrounding the electrode from which the electrical signal emanates, the change in lead impedance over a cardiac cycle is indicative of the volume of blood that is being pumped by the heart. The data in FIG. 5 demonstrates this principle in that the change in impedance measured in the animal subject during an induced ventricular fibrillation (0.75 ohms) is significantly less than the change in impedance (1.67 ohms) measured during normal sinus rhythm. Consequently, the microprocessor 112 can use the delta impedance value provided by the impedance measurement circuit 140 as a further sensor input to regulate the activity of the heart 104. Moreover, the microprocessor 112 can be adapted to store the delta impedance value in the memory 126 so that this value can be provided to a treating physician during subsequent follow up visits as further diagnostic information for the physician as to the function of the heart 104.

Hence, the impedance measurement circuit 140 of the preferred embodiment advantageously combines the measuring of the lead impedance, to determine whether a particular lead 106 has been damaged, with the measurement of impedance changes over time, which is indicative of the stroke volume of the heart. The microprocessor 112 may be able to use this hemodynamic parameter to optimize the delivery of therapeutic electrical stimulation to the heart 104 and may also record this hemodynamic parameter in the memory 126 for subsequent review by the treating physician via the telemetry circuit 130.

Advantageously, the ability to accurately measure the lead impedance using a low power technique enables the implantable cardiac stimulating device 100 to frequently test the lead impedance of the high voltage leads 106 and the RV and SVC coils 160, 170 for possible damage. Consequently, when the lead impedance is indicative of a particular problem, the microprocessor 112 can take corrective action to disable the defective electrode and may also provide a warning signal to the patient via the annunciator 132 so as to induce the patient to return to the physician to seek corrective action.

Figure 6:
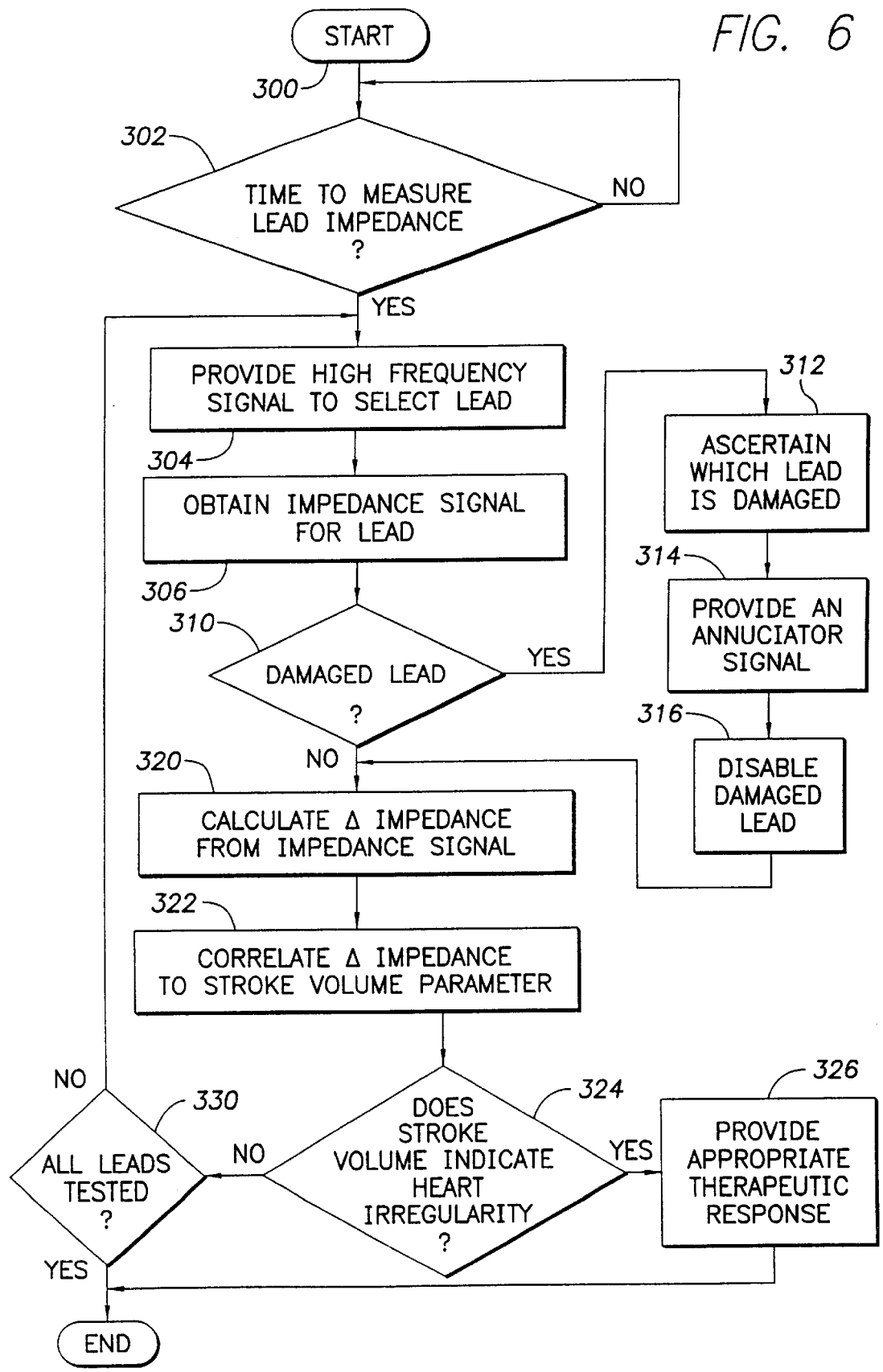
FIG. 6 is an exemplary flow chart illustrating the operation of the microprocessor of the implantable cardiac stimulating device of FIG. 1 as it implements an impedance measurement process of the preferred embodiment.

FIG. 6 is a flow chart which illustrates the operation of the implantable cardiac stimulating device 100 as it assesses the impedance of the SVC coil 170 and the RV electrode 160 via their associated leads 106 and takes corrective action upon determining that the tested lead is damaged.

As shown in FIG. 6, the microprocessor 112, from a start state 300, determines, in decision state 302, whether the time period for measuring the lead impedance has occurred. As discussed above, the microprocessor 112 is adapted to periodically measure the impedance of each of the high voltage leads 106 and the associated coils 160, 170. In one embodiment, the microprocessor 112 is adapted to perform this lead impedance measurement on each of the leads 106 and coils 160, 170 on a daily basis, however, it will be appreciated that the frequency with which the impedance is measured can be varied based on a number of factors.

For example, if previous measurements of lead impedance indicate that the impedance is increasing, thereby indicating that the lead may be degrading over time, it may be desirable to increase the rate at which the lead impedance is measured so that the likelihood of undetected lead failure occurring between impedance measurements is reduced. If the microprocessor 112 determines, in decision state 302, that the time to measure lead impedance has occurred, the microprocessor 112 then, in state 304, provides the high frequency, low amplitude impedance measurement signal to the selected lead 106 for the preselected period of time. In particular, the microprocessor 112 induces the current source 200 of the impedance measurement circuit 140 to provide a high frequency, low amplitude, e.g., 50 KHz signal at 100 or 500 microamps, to the selected lead 106. This signal is provided for a selected duration of time which preferably exceeds several heart cycles, e.g., 10 seconds.

The impedance measurement circuit 140, in step 306, samples the resulting electrical voltage between the high voltage leads 160 and 170 or can 110. In the preferred embodiment, the resulting electrical response, which is indicative of the lead impedance, is measured from one of the leads 106 to the other lead 106 or to the casing 110 of the implantable cardiac stimulating device 100. This provides an indication as to the impedance of the selected lead 106 and the selected coil 160,170 which the microprocessor 112 can then use to determine, in decision state 310, whether the lead 106 and the associated coil 160, 170 has been damaged.

The determination as to whether a particular lead and associated coil has been damaged is made by the microprocessor 112 by comparing the impedance measurement obtained in state 306 to a preselected maximum or minimum impedance value for the particular lead and coil. It will be appreciated that a catastrophic failure of the lead, e.g., a broken lead, will generally be detected as an extremely high or infinite impedance. However, damage to the lead may be indicated by a small rise in the lead impedance exceeding the maximum selected lead impedance for the particular lead. While this problem may not be as serious as a broken lead, the increase in lead impedance may result in attenuation of the high voltage waveform that is to be applied to the heart 104 when the microprocessor 112 determines that a cardioversion or defibrillation waveform should be applied to the heart 104. Also, damage to the insulator material within the lead may cause a drop in lead impedance, possibly below a minimum preselected value.

Consequently, if the microprocessor 112 determines, in decision state 310, that the lead is damaged, the microprocessor 112 then proceeds to take corrective action to minimize the danger posed by the damaged lead. In one application, the corrective action may comprise providing higher magnitude therapeutic waveforms to the heart upon a subsequent detection of a heart arrhythmia to overcome the rise in impedance, or, as illustrated in the flow chart of FIG. 6, may comprise disabling a particular damaged lead 106.

In particular, the microprocessor 112, in a state 312, ascertains which of the leads 106 is damaged. Subsequently, the microprocessor 112 then induces the annunciator 132 to provide an annunciator signal to the patient so that the patient can be advised of the need to return to a treating physician for follow-up care. As discussed above, the annunciator 132 may be comprised of a piezo-electric buzzer or the like which would provide an audible tone to the patient indicative of the problem. Alternatively, the annunciator 132 may be comprised of providing a series of electrical stimulations to the patient that are adapted to be felt by the patient without stimulating the heart 104. Once the annunciator 132 has been activated, in state 314, the microprocessor 112 can then proceed to state 316 to disable the damaged lead.

The lead impedance measurements provided by the present invention can also be used for fine tuning of therapy. Specifically, small changes in impedance may not indicate lead failure but may indicate lead maturation. In such a case, it may be advantageous to fine tune the defibrillation waveform duration to more advantageously match the new lead impedance. For example, in the preferred embodiment of the implantable cardiac stimulating device 100, when an arrhythmia is detected, the microprocessor 112 provides a high voltage, biphasic waveform that emanates from the RV coil 160 and both the casing 110 and the SVC electrode 170 are configured to be the return electrodes. However, if the SVC coil 170 and the associated high voltage lead 106 is damaged, and the damage is indicative of the SVC electrode being shorted together with the RV electrode, providing a therapeutic waveform under these circumstances may result in the overall device being subsequently unable to provide therapeutic waveforms to the heart 104. This particular problem would be detected by the microprocessor 112 when the impedance measured in state 306 following the delivery of the low amplitude, high frequency test pulse, is very low or zero. To avoid this problem, if this particular condition is detected, the microprocessor 112 is adapted to disable, in state 316, the SVC electrode as a return electrode for a defibrillation or cardioversion waveform that is emitted from the RV coil 160 and the conductive casing 110 can be used in its place as the return electrode.

After taking the appropriate corrective action, the microprocessor 112 then proceeds in state 320 to review the change in impedance, i.e., the delta impedance, from the impedance signal that is provided by the impedance measurement circuit 140. As discussed above, the change in impedance over the duration of the high frequency, low voltage impedance measuring current, provides an indication of stroke volume which is a valuable hemodynamic parameter. The microprocessor 112 can then correlate the change in impedance to the stroke volume parameter in state 322 and then determine, in decision state 324, whether the stroke volume parameter is indicative of a heart irregularity. In the event that the stroke volume parameter is indicative of a particular heart irregularity, the microprocessor 112 can be adapted to take appropriate corrective action in state 326. The appropriate corrective action may consist of applying a therapeutic electrical stimulation or, in the alternative, may comprise reconfiguring the therapeutic electrical stimulations that are to be provided to the heart 104. Moreover, the microprocessor 112 may simply just record the stroke volume parameter for subsequent review by the treating physician.

In the event that the change in impedance is not indicative of a heart irregularity, the microprocessor 112 then determines, in decision state 330, whether all of the leads 106 and associated electrodes 160, 170 have been tested. In the event that the leads 106 have not been tested, the microprocessor 112 then returns to state 304 where the high frequency signal is provided to the next selected lead.

Consequently, it will be appreciated that, by applying a high frequency, low amplitude signal to periodically measure lead impedance, a lead impedance measurement can be obtained for each of the leads which has a high degree of correlation to the actual lead impedance that would occur when a high voltage waveform is applied to the heart via the selected lead. This parameter can therefore be used to determine whether particular circumstances exist with the leads that require corrective action. The circumstances may comprise a short between the SVC and RV leads which would prompt the microprocessor to disable the SVC lead so as to preserve the operational functionality of the device. Moreover, using the high frequency, low amplitude current signal to measure the impedance also results in very accurate lead impedance measurements being obtained without the consumption of excessive power from the battery. The high degree of correlation between the impedance measurement obtained using the high frequency, low amplitude signal avoids the difficulties associated with measuring lead impedance using low voltage, low frequency signals, e.g., being unable to accurately detect changes in lead impedance.

Although the preferred embodiment of the present invention has shown, described and pointed out the fundamental novel features of the invention as applied to these embodiments, it will be understood that various omissions, substitutions, and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. An implantable cardiac stimulation device enclosed in a conductive housing and adapted for use with at least one cardiac lead suitable for shocking a patient's heart, the device further adapted to detect lead fractures that would prevent a high voltage shock to a patient's heart, the device comprising:

a current generator coupled to said lead and adapted to supply an impedance measuring current to the lead, said current being of a relatively low amplitude and a relatively high frequency;

a return in electrical communication with the current generator and the lead and forming thereby a current return path between the lead and the current generator; and an impedance measuring circuit coupled to the lead and return such that upon the supply of the impedance measuring current to the lead the impedance measurement circuit measures the impedance between the lead and the return.

2. The device of claim 1 wherein the current generator generates an impedance measuring current having a frequency in the range from 20 kHz to 50 kHz and an amplitude of no greater than about 500 ua.

3. The device of claim 1 wherein the return comprises the conductive housing and wherein the housing is in electrical communication with the current generator.

4. The device of claim 1 wherein the at least one cardiac lead comprises two leads and the current generator is adapted to be coupled to each one of the two leads and wherein the return comprises one of the leads.

5. The device of claim 1 wherein the impedance measuring circuit includes a voltage measurement circuit coupled across the lead and the return to measure the voltage therebetween and wherein the impedance measuring circuit determines a lead impedance signal based upon the measured voltage and the value of the supplied impedance measuring current.

6. The device of claim 5 wherein the impedance measuring circuit includes a band pass filter having a center frequency essentially equal to the frequency of the impedance measuring current to filter the lead impedance signal and provide thereby a band passed signal.

7. The device of claim 6 wherein the impedance measuring circuit includes a demodulator to demodulate the band passed signal for providing a demodulated signal representative of the lead impedance.

8. The device of claim 7 further comprising a processor configured to receive the demodulated signal and determine the change in lead impedance and correlate cardiac stroke volume to such impedance change.

9. The device of claim 8 further comprising a pulse generator configured to deliver therapeutic electrical stimulation to a patient's heart, via the at least one cardiac lead, as a function of cardiac stroke volume.

10. The device of claim 7 wherein the processor is adapted to vary the magnitude of the therapeutic electrical stimulation delivered by the pulse generator such that when the lead impedance exceeds a preselected value the processor causes the pulse generator to increase the magnitude of said stimulation.

11. The device of claim 8 wherein the processor is adapted to disable the at least one cardiac lead such that when the lead impedance exceeds a preselected maximum value the processor causes the lead to be disabled.

12. The device of claim 8 further comprising an annunciator wherein the processor is further adapted to cause the annunciator to provide notification when the lead impedance exceeds a predetermined maximum value and when the lead impedance falls below a predetermined minimum value.

13. The device of claim 8 wherein the processor is adapted to take corrective action such that when the lead impedance is of a value that damage to the lead is indicated, the processor causes such corrective to be taken.

14. In a cardiac stimulation device enclosed in an electrically conductive housing and configured for use with at least one cardiac lead suitable for shocking a patient's heart and a current return, a method of determining the impedance of such lead to detect lead fractures that would prevent a high voltage shock to a patient's heart, the method comprising the steps of:
applying an impedance measuring current, having a relatively low amplitude and a relatively high frequency, to the lead and return;
measuring the resultant voltage across the lead and return; and
determining the lead impedance based upon the value of the impedance measuring current and the resultant voltage across the lead and return.

15. The method of claim 14 wherein the step of applying an impedance measuring current further comprises the step of applying a current having a frequency in the range from 20 kHz to 50 kHz.

16. The method of claim 14 wherein the step of applying an impedance measuring current further comprises the step of applying a current having an amplitude of no greater than 500 ua.

17. The method of claim 14 wherein the return comprises the conductive housing and the step of determining the lead impedance includes the step of measuring the voltage across the lead and the conductive housing.

18. The method of claim 14 wherein the at least one cardiac lead comprises two leads and the return comprises one of the leads and the step of applying the impedance measuring current comprises the step of applying the current to said two leads.

19. The method of claim 18 wherein the step of measuring the resultant voltage comprises the step of measuring the voltage across said two leads.

20. The method of claim 19 wherein the step of determining the lead impedance comprises the step of determining said impedance based upon the value of the impedance measuring current and the voltage across said two leads.

21. The method of claim 20 wherein the step of determining the lead impedance further produces an impedance signal representative of the lead impedance, the method further comprising the step of filtering said impedance signal through a band pass filter having a center frequency essentially equal to the frequency of the impedance measuring current.

22. The method of claim 21 further comprising the step of utilizing a band pass filter having a center frequency of a value that the effect of any Warberg capacitance on the lead impedance measurement is minimized.

23. The method of claim 21 further comprising the step of demodulating the impedance signal after it has been filtered to obtain a signal representative of the lead impedance and a change in lead impedance.

24. The method of claim 23 further comprising the step of correlating cardiac stroke volume to the change in lead impedance.

25. The method of claim 24 wherein the cardiac stimulation device includes a pulse generator configured to deliver therapeutic electrical stimulation to a patient's heart via the at least one cardiac lead, the method further comprising the step of delivering therapeutic electrical stimulation to said heart as a function of cardiac stroke volume.

26. The method of claim 14 further comprising the steps of:
comparing the lead impedance to a preselected maximum value and a preselected minimum value; and
taking corrective action when the lead impedance either exceeds the preselected maximum value or is less than the preselected minimum value.

27. The method of claim 26 comprising the step of providing an annunciator signal when a lead impedance exceeds a predetermined maximum value or is less than a predetermined minimum value.

28. An implantable cardiac stimulation device enclosed in a conductive housing and adapted for use with cardiac lead means, the device further adapted to measure the impedance of said lead means, the device comprising:
means for supplying an impedance measuring current, having a relatively low amplitude and a relatively high frequency, to the lead means; and
means for determining the lead impedance based upon the supply of impedance measuring current to the lead means.

29. The device of claim 28 further comprising impedance measuring current return means wherein the supplying means supplies impedance measuring current to the lead means and said return means.

30. The device of claim 29 further comprising means for measuring a voltage across the return means and the lead means.

31. The device of claim 30 wherein the determining means includes means for calculating the lead impedance based upon the value of the impedance measuring current and the voltage across the return means and the lead means and for providing a lead impedance signal thereby.

32. The device of claim 31 wherein the return means comprises the conductive housing.

33. The device of claim 31 wherein the lead means comprises a pair of leads and said return means comprises one of the leads and the voltage measuring means measures the voltage across the return means and the other lead.

34. The device of claim 31 further comprising annunciator means for providing notification when the lead impedance exceeds a preselected maximum value and when the lead impedance signal falls below a preselected minimum value.

35. The device of claim 31 wherein the calculating means includes:

band pass filter means having a center frequency essentially equal to the frequency of the impedance measuring current for filtering the lead impedance signal and for providing thereby a band passed signal; and demodulator means for demodulating the band passed signal for providing a parameter representative of the lead impedance.

36. The device of claim 35 wherein the cardiac stimulation device further comprises:

pulse generator means for delivering therapeutic electrical stimulation to a patient's heart via the lead means; and means for adjusting the electrical stimulation to said heart as a function of said parameter.

37. The device of claim 35 further comprising means for disabling a respective lead, when said parameter corresponding to said respective lead, exceeds a preselected maximum value or is less than a preselected minimum value.

38. The device of claim 28 wherein the supplying means supplies an impedance measuring current having a magnitude of no greater than 500 ua.

39. The device of claim 28 wherein the supplying means supplies an impedance measuring current having a frequency in the range from 20 kHz to 50 kHz.

* * * * *